United States Patent
Lech

(10) Patent No.: US 11,344,359 B2
(45) Date of Patent: *May 31, 2022

(54) WAKE-UP SYSTEM AND METHOD FOR POWERED SURGICAL INSTRUMENTS

(71) Applicant: Covidien LP, Mansfield, MA (US)

(72) Inventor: Richard Lech, Hamden, CT (US)

(73) Assignee: Covidien LP, Mansfield, MA (US)

( * ) Notice: Subject to any disclaimer, the term of this patent is extended or adjusted under 35 U.S.C. 154(b) by 30 days.

This patent is subject to a terminal disclaimer.

(21) Appl. No.: 16/903,695

(22) Filed: Jun. 17, 2020

(65) Prior Publication Data

US 2020/0305955 A1     Oct. 1, 2020

Related U.S. Application Data

(60) Continuation of application No. 15/841,831, filed on Dec. 14, 2017, now Pat. No. 10,722,290, which is a
(Continued)

(51) Int. Cl.
*G06F 1/3203*       (2019.01)
*A61B 18/14*        (2006.01)
(Continued)

(52) U.S. Cl.
CPC ........ *A61B 18/14* (2013.01); *A61B 17/07207* (2013.01); *A61B 18/1206* (2013.01);
(Continued)

(58) Field of Classification Search
CPC .............. A61B 18/14; A61B 17/07207; A61B 18/1206; A61B 90/98; A61B 2090/0808;
(Continued)

(56) References Cited

U.S. PATENT DOCUMENTS

| | | |
|---|---|---|
| 5,025,968 A | 6/1991 | Nasiatka |
| 5,400,267 A | 3/1995 | Denen et al. |
| | (Continued) | |

FOREIGN PATENT DOCUMENTS

| | | |
|---|---|---|
| EP | 2772206 A2 | 9/2014 |
| WO | 2011012041 A1 | 2/2011 |
| | (Continued) | |

OTHER PUBLICATIONS

European Search Report dated Sep. 29, 2015, issued in European Application No. 15166106.
(Continued)

*Primary Examiner* — Volvick Derose
(74) *Attorney, Agent, or Firm* — Carter, DeLuca & Farrell LLP

(57) ABSTRACT

The present disclosure is directed to an electromechanical surgical system having an end effector and an adapter assembly for selectively interconnecting the end effector and a hand-held surgical instrument. A one-wire bidirectional serial communications interface or bus extends through the end effector, the adapter assembly, and the hand-held surgical instrument. The hand-held surgical instrument includes a master circuit coupled to the bus and configured to identify or control the adapter assembly or the end effector. A power source is couplable to the bus and configured to provide power to the adapter assembly or the end effector. A first switch connects the master circuit to the bus and a second switch connects the power source to the bus. A processor controls operation of the hand-held surgical instrument. The controller has a wake-up pin connected to the bus and is configured to receive a presence pulse from the adapter or end effector.

18 Claims, 3 Drawing Sheets

Related U.S. Application Data division of application No. 14/269,843, filed on May 5, 2014, now Pat. No. 9,872,722.

(51) Int. Cl.

| | | |
|---|---|---|
| *A61B 18/12* | (2006.01) | |
| *A61B 17/072* | (2006.01) | |
| *A61B 17/00* | (2006.01) | |
| *A61B 90/98* | (2016.01) | |
| *A61B 90/00* | (2016.01) | |

(52) U.S. Cl.
CPC ....... *A61B 90/98* (2016.02); *A61B 2017/0046* (2013.01); *A61B 2017/00137* (2013.01); *A61B 2017/00398* (2013.01); *A61B 2017/00473* (2013.01); *A61B 2017/00482* (2013.01); *A61B 2017/00734* (2013.01); *A61B 2018/1226* (2013.01); *A61B 2090/0808* (2016.02); *G06F 1/3203* (2013.01)

(58) Field of Classification Search
CPC .. A61B 2017/00473; A61B 2017/0046; A61B 2017/00137; A61B 2017/00734; A61B 2017/00482; A61B 2017/00398; A61B 2018/1226
USPC .......................................................... 713/323
See application file for complete search history.

(56) References Cited

U.S. PATENT DOCUMENTS

| | | | |
|---|---|---|---|
| 5,675,811 A * | 10/1997 | Broedner | G06F 13/4291 710/104 |
| 6,166,496 A | 12/2000 | Lys et al. | |
| 6,211,626 B1 | 4/2001 | Lys et al. | |
| 6,292,901 B1 | 9/2001 | Lys et al. | |
| 6,340,868 B1 | 1/2002 | Lys et al. | |
| 6,459,919 B1 | 10/2002 | Lys et al. | |
| 6,528,954 B1 | 3/2003 | Lys et al. | |
| 6,577,080 B2 | 6/2003 | Lys et al. | |
| 6,720,745 B2 | 4/2004 | Lys et al. | |
| 6,955,281 B1 | 10/2005 | Wei | |
| 7,013,178 B2 | 3/2006 | Reinke et al. | |
| 7,038,398 B1 | 5/2006 | Lys et al. | |
| 7,132,804 B2 | 11/2006 | Lys et al. | |
| 7,139,613 B2 | 11/2006 | Reinke et al. | |
| 7,180,252 B2 | 2/2007 | Lys et al. | |
| 7,214,230 B2 | 5/2007 | Brock et al. | |
| 7,221,104 B2 | 5/2007 | Lys et al. | |
| 7,308,296 B2 | 12/2007 | Lys et al. | |
| 7,352,339 B2 | 4/2008 | Morgan et al. | |
| 7,453,217 B2 | 11/2008 | Lys et al. | |
| 7,525,254 B2 | 4/2009 | Lys et al. | |
| 7,598,686 B2 | 10/2009 | Lys et al. | |
| 7,865,250 B2 | 1/2011 | Mrva et al. | |
| 8,390,456 B2 | 3/2013 | Puleston et al. | |
| 8,517,241 B2 * | 8/2013 | Nicholas | A61B 17/068 227/175.3 |
| 8,702,748 B2 | 4/2014 | Kim et al. | |
| 8,733,614 B2 * | 5/2014 | Ross | A61B 90/98 227/179.1 |
| 9,872,722 B2 | 1/2018 | Lech | |
| 10,722,290 B2 | 7/2020 | Lech | |
| 2001/0028227 A1 | 10/2001 | Lys et al. | |
| 2002/0047646 A1 | 4/2002 | Lys et al. | |
| 2002/0087169 A1 | 7/2002 | Brock et al. | |
| 2002/0113555 A1 | 8/2002 | Lys et al. | |
| 2003/0005786 A1 | 1/2003 | Stuart et al. | |
| 2003/0011538 A1 | 1/2003 | Lys et al. | |
| 2003/0076281 A1 | 4/2003 | Morgan et al. | |
| 2003/0100837 A1 | 5/2003 | Lys et al. | |
| 2004/0059396 A1 | 3/2004 | Reinke et al. | |
| 2004/0122490 A1 | 6/2004 | Reinke et al. | |
| 2004/0153124 A1 | 8/2004 | Whitman | |
| 2004/0155609 A1 | 8/2004 | Lys et al. | |
| 2004/0257007 A1 | 12/2004 | Lys et al. | |
| 2005/0063194 A1 | 3/2005 | Lys et al. | |
| 2005/0151489 A1 | 7/2005 | Lys et al. | |
| 2006/0074415 A1 | 4/2006 | Scott et al. | |
| 2006/0079889 A1 | 4/2006 | Scott | |
| 2006/0149345 A1 | 7/2006 | Boggs et al. | |
| 2006/0173507 A1 | 8/2006 | Mrva et al. | |
| 2007/0060955 A1 | 3/2007 | Strother et al. | |
| 2007/0060967 A1 | 3/2007 | Strother et al. | |
| 2007/0060968 A1 | 3/2007 | Strother et al. | |
| 2007/0060979 A1 | 3/2007 | Strother et al. | |
| 2007/0060980 A1 | 3/2007 | Strother et al. | |
| 2007/0066995 A1 | 3/2007 | Strother et al. | |
| 2007/0067000 A1 | 3/2007 | Strother et al. | |
| 2007/0135803 A1 | 6/2007 | Belson | |
| 2007/0188427 A1 | 8/2007 | Lys et al. | |
| 2008/0183081 A1 | 7/2008 | Lys et al. | |
| 2008/0217391 A1 | 9/2008 | Roof et al. | |
| 2008/0248685 A1 * | 10/2008 | Sartor | A61B 18/1206 439/489 |
| 2009/0090763 A1 | 4/2009 | Zemlok et al. | |
| 2010/0076429 A1 * | 3/2010 | Heinrich | A61B 17/115 606/49 |
| 2010/0134257 A1 | 6/2010 | Puleston et al. | |
| 2010/0191250 A1 | 7/2010 | Scott et al. | |
| 2010/0211053 A1 | 8/2010 | Ross et al. | |
| 2010/0280543 A1 | 11/2010 | Kim et al. | |
| 2011/0004225 A1 | 1/2011 | Choi et al. | |
| 2011/0017801 A1 * | 1/2011 | Zemlok | A61B 17/07207 227/175.1 |
| 2011/0105945 A1 | 5/2011 | Videbaek et al. | |
| 2012/0080477 A1 | 4/2012 | Leimbach et al. | |
| 2012/0089131 A1 * | 4/2012 | Zemlok | A61B 17/115 606/1 |
| 2012/0109154 A1 | 5/2012 | Ross et al. | |
| 2013/0067725 A1 * | 3/2013 | Behnke, II | A61B 18/1815 29/592.1 |
| 2013/0176115 A1 | 7/2013 | Puleston et al. | |
| 2013/0191513 A1 | 7/2013 | Kamen et al. | |
| 2013/0297330 A1 | 11/2013 | Kamen et al. | |
| 2013/0317753 A1 | 11/2013 | Kamen et al. | |
| 2013/0324979 A1 | 12/2013 | Nicholas et al. | |
| 2014/0001224 A1 * | 1/2014 | McNeill | B25F 5/00 227/1 |
| 2015/0272574 A1 * | 10/2015 | Leimbach | A61B 17/068 713/323 |
| 2015/0272575 A1 * | 10/2015 | Leimbach | A61B 90/98 227/175.3 |
| 2015/0313665 A1 | 11/2015 | Lech | |
| 2016/0066911 A1 | 3/2016 | Baber et al. | |
| 2016/0066912 A1 | 3/2016 | Baber et al. | |

FOREIGN PATENT DOCUMENTS

| | | | | |
|---|---|---|---|---|
| WO | WO-2011012041 A1 * | 2/2011 | ......... | G06F 13/4291 |
| WO | 2013018926 A1 | 2/2013 | | |

OTHER PUBLICATIONS

Japanese Office Action dated Feb. 4, 2019 issued in corresponding JP Appln. No. 2015-064119.
Australian Examination Action dated Feb. 11, 2019 issued in corresponding AU Appln. No. 2015200959.
Canadian Office Action issued in Canadian Patent Application No. 2,883,154, dated Apr. 16, 2021.
Canadian Office Action issued in corresponding Candian Application No. 2,883,154 dated Sep. 21, 2021, 5 pages.

* cited by examiner

WAKE-UP SYSTEM AND METHOD FOR POWERED SURGICAL INSTRUMENTS

CROSS-REFERENCE TO RELATED APPLICATION

This application is a continuation of U.S. patent application Ser. No. 15/841,831, filed on Dec. 14, 2017, which is a divisional of U.S. patent application Ser. No. 14/269,843, filed on May 5, 2014, now U.S. Pat. No. 9,872,722 the entire contents of each of which are incorporated by reference herein.

BACKGROUND

Technical Field

The present disclosure relates to surgical instruments, devices and/or systems for performing minimally invasive surgical procedures and methods of use thereof. More specifically, the present disclosure relates to systems and methods for transitioning a powered surgical instrument from a sleep state to an active state.

Description of Related Art

A number of surgical instrument manufacturers have developed product lines with proprietary drive systems for operating and/or manipulating electromechanical surgical instruments. Some electromechanical surgical instruments include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

In order to preserve battery life, all or some of the components of the electromechanical surgical instrument are placed in a sleep mode when the instrument is not in use. In order to place the instrument in an active state, the electromechanical surgical instrument needs to poll a separate pin or line to determine whether a component of the electromechanical surgical instrument has been attached to the handle assembly. In order to poll the separate pin or line, a processor in the surgical instrument needs to periodically wake-up, thus shortening the battery life. Further, the processor is required to interrogate the bus to determine if a component has been attached to the surgical instrument in order to transition the instrument into an active state.

SUMMARY

An electromechanical surgical system is provided in an aspect of the present disclosure. The system includes an end effector configured to perform at least one function and an adapter assembly being arranged for selectively interconnecting the end effector and a hand-held surgical instrument. A one-wire bidirectional serial communications interface extends through the end effector, the adapter assembly, and the hand-held instrument. The hand-held surgical instrument has an instrument housing defining a connecting portion for selectively connecting with the adapter assembly. The hand-held surgical instrument includes a master circuit coupled to the one-wire bidirectional serial communications interface and configured to identify or control the adapter assembly or the end effector. A power source is coupled to the one-wire bidirectional serial communications interface and is configured to provide power to the adapter assembly or the end effector. A first switch connects the master circuit to the one-wire bidirectional serial communications interface and a second switch connects the power source to the one-wire bidirectional serial communications interface. A processor controls operation of the hand-held surgical instrument. The processor has a wake-up pin connected to the one-wire bidirectional serial communications interface. The wake-up pin is configured to receive a presence pulse from the end effector or the adapter.

In some embodiments, the first switch is connected to a first pin of the processor and the second switch is connected to a second pin on the processor. If the processor is in a sleep state, the processor transmits a first signal on the first pin to disconnect the master circuit from the one-wire bidirectional serial communications interface. The processor also transmits a second signal on the second pin to connect the power source to the one-wire bidirectional serial communications interface.

In some embodiments, the adapter assembly generates the presence pulse when the adapter assembly is connected to the hand-held instrument. The processor transitions from the sleep state to an active state when the wake-up pin receives the presence pulse. The adapter assembly includes an integrated circuit having an identification code stored thereon which is transmitted to the master circuit after the processor is placed in the active state and the master circuit requests the identification code from the adapter assembly.

In other embodiments, the end effector generates the presence pulse when the end effector is connected to the hand-held instrument. The processor transitions from the sleep state to an active state when the wake-up pin receives the presence pulse. The end effector includes an integrated circuit having an identification code stored thereon which is transmitted to the master circuit after the processor is placed in the active state and the master circuit requests the identification code from the end effector.

In another aspect of the present disclosure, a method for waking up an electromechanical surgical system having a housing that is couplable to a slave device is provided. In the method, a one-wire master circuit is disconnected from a one-wire bidirectional serial communications interface while a power source is connected to the one-wire bidirectional serial communications interface. The system detects a presence pulse from the slave device and if the presence pulse is detected, the electromechanical surgical system is placed in an active state.

In some embodiments, the slave device is an adapter, a single use loading unit, or a multi-use loading unit.

In some embodiments, the method also includes interrogating the one-wire bidirectional serial communications interface for the slave device when the electromechanical surgical system is placed in the active state.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
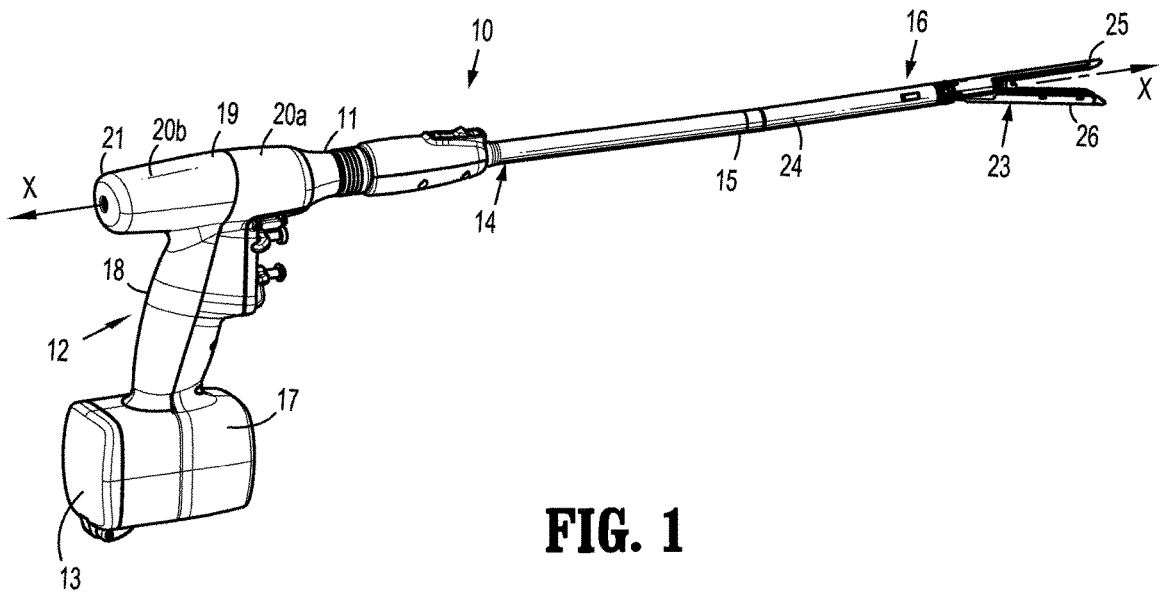
FIG. 1 is a perspective view of a surgical stapling instrument for use with a chip assembly according to embodiments of the present disclosure.

Embodiments of the presently disclosed electromechanical surgical system, instrument and/or device are described in detail with reference to the drawings, in which like reference numerals designate identical or corresponding elements in each of the several views.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A or B" means "(A), (B), or (A and B)". For the purposes of this description, a phrase in the form "at least one of A, B, or C" means "(A), (B), (C), (A and B), (A and C), (B and C), or (A, B and C)".

The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is farther away from the clinician.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include Field Programmable Gate Arrays (FPGA) and Complex Programmable Logic Devices (CPLD). The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, VHDL, Verilog, metalanguages which themselves specify programs, and all first, second, third, fourth, and fifth generation computer languages. Also included are database and other data schemas, and any other metalanguages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, optical signals, digital signals, and by other like signals.

As used herein, the term "slave device" may refer to any device that is attached a powered surgical instrument. For example, a slave device may be an adapter, a clamshell, single use loading unit (SULU), a multi-use loading unit (MULU), etc. In the embodiments described herein, each slave device includes a chip that initiates a presence pulse which will be described below.

In embodiments described herein, a powered surgical instrument is couplable to interchangeable adapters and different loading units. For example, the loading units may be a SULU or a MULU. The powered surgical instrument has a handle that includes a processor which controls operation of the powered surgical instrument. The processor can be placed in a sleep state to conserve battery life and transitioned into an active state when one or more slave devices are attached to the instrument. When one or more slave devices are connected to the instrument, the slave devices generate a presence pulse that is transmitted via a one-wire bidirectional serial communication interface to a wake-up pin on the processor. As such, the processor does not need to wake-up on its own thereby saving power. Further, the processor does not need to interrogate a bus on any other type of wake-up condition, which saves time. Additionally, the need for an extra pin going to a distal slave device or any external logic required to generate a wake-up signal is eliminated.

Figure 2:
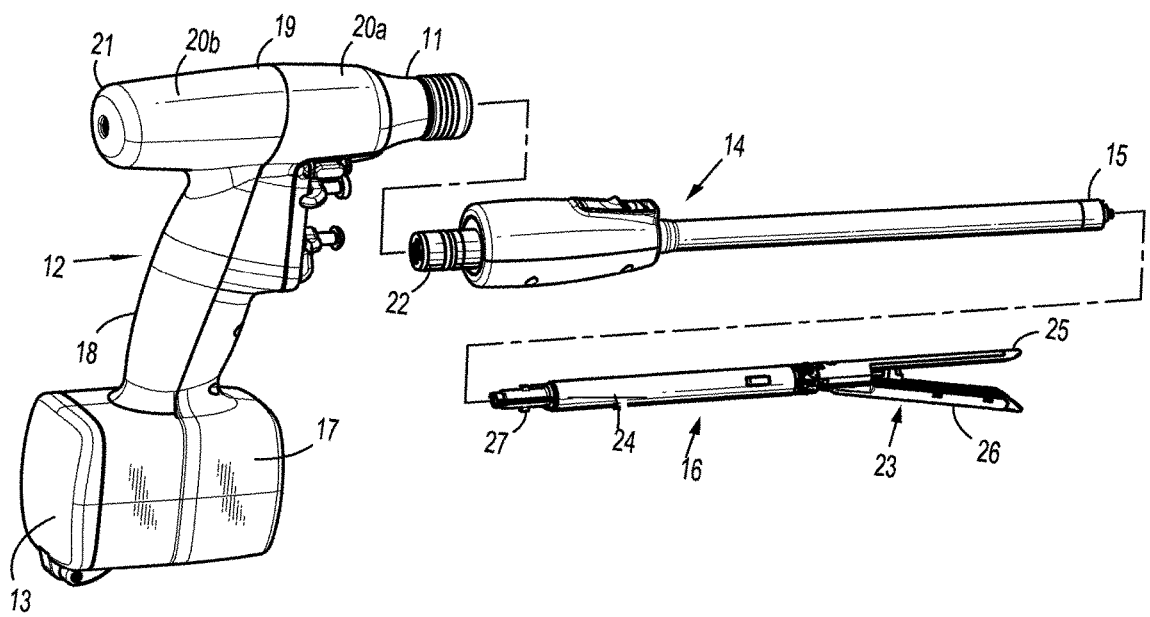
FIG. 2 is a perspective view of the surgical stapling instrument of FIG. 1 showing the handle assembly, adapter assembly, and loading unit in a separated configuration.

With reference initially to FIGS. 1 and 2, a powered surgical instrument including a one-wire bidirectional serial communication system according to the present disclosure is shown generally as stapler 10. Stapler 10 includes a handle assembly 12, an adapter assembly 14 extending distally from handle assembly 12, and a loading unit 16 selectively secured to a distal end of adapter assembly 14. A detailed description of handle assembly 12, adapter assembly 14, and loading unit 16 is provided in commonly-owned U.S. Patent Appl. Publ. No. 2012/0089131, the contents of which is incorporated herein by reference in its entirety.

Handle assembly 12 includes a lower housing portion 17, an intermediate housing portion 18 extending from and/or supported on lower housing portion 17, and an upper housing portion 19 extending from and/or supported on intermediate housing portion 18. Intermediate housing portion 18 and upper housing portion 19 are separated into a distal half-section 20a that is integrally formed with, and extends from, the lower housing portion 17, and a proximal half-section 20b joined to distal half-section 20a by any suitable manner of attachment, such as without limitation, ultrasonic welding and/or a plurality of fasteners. When joined, distal and proximal half-sections 20a, 20b form a handle housing 21 defining a cavity therein which houses a circuit board that includes a controller (not shown), and a drive mechanism (not shown).

Lower housing portion 17 includes a door 13 pivotally connected thereto for accessing a cavity formed in lower housing portion 17 for retaining a battery (not shown) therein. It is contemplated that stapler 10 may be powered by any number of power sources, such as, for example and without limitation, a fuel cell, a power cord connected to an external power source, and so forth.

Adapter assembly 14 includes a drive coupler 22 at a proximal end thereof and coupled to a loading unit coupler 15 at a distal end thereof. Distal half-section 20a of upper housing portion 19 defines a nose or connecting portion 11 configured to operably receive drive coupler 22 of adapter assembly 14. Loading unit 16 includes an adapter coupler 27 configured to operably receive loading unit coupler 15 of adapter assembly 14.

Upper housing portion 19 of handle housing 21 encloses a drive mechanism (not shown) configured to drive shafts and/or gear components (not shown) in order to perform the various operations of stapler 10. In particular, the drive mechanism is configured to drive shafts and/or gear components in order to selectively move a tool assembly 23 of loading unit 16 relative to a proximal body portion 24 of loading unit 16, to rotate loading unit 16 about a longitudinal axis "X-X" (FIG. 1) relative to handle housing 21, to move an anvil assembly 25 relative to cartridge assembly 26 of loading unit 16, and/or to fire a stapling and cutting cartridge within cartridge assembly 26 of loading unit 16.

Figure 3:
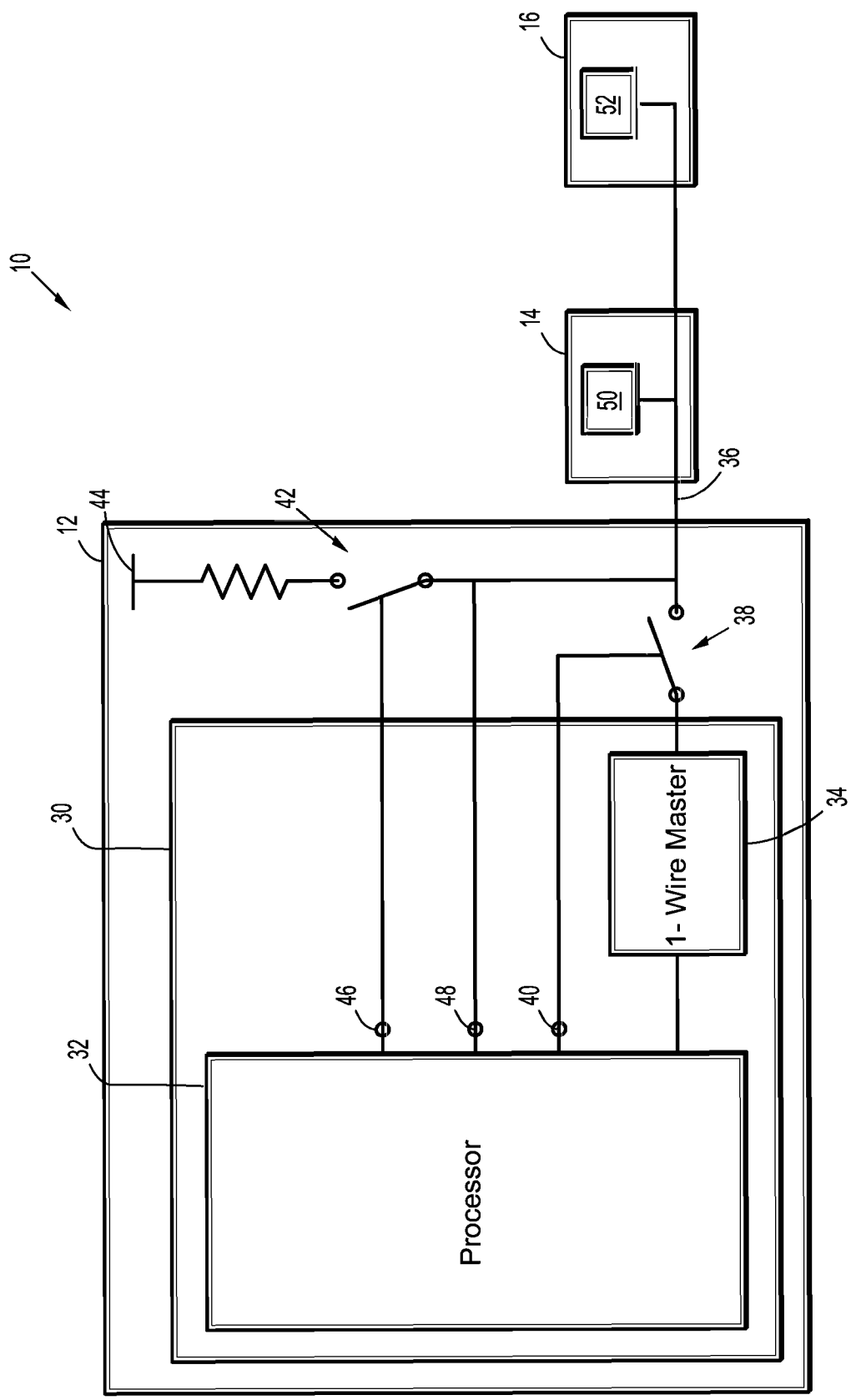
FIG. 3 is a system block diagram of the surgical stapling instrument of FIG. 1.

Turning to FIG. 3, handle assembly 12 includes a controller 30 that controls operation of the stapler 10. Controller 30 includes a processor 32 and a one-wire master circuit 34. When stapler 10 is not in use, processor 32 is placed in a sleep state to conserve battery life. The processor 32 may transition from a sleep state to an active state upon an instruction from a clinician, attaching an adapter 14 to the handle assembly 12, or attaching a loading unit 16 to an adapter 14 that is already coupled to the handle assembly 12.

The one-wire master circuit 34 is the main controller of a one-wire bidirectional serial communications interface or bus 36 and is responsible for finding slave devices on the bus 36 when the slave device(s) announce their presence. The one-wire master circuit 34 also issues commands to the slave devices. There may be only one master circuit 34 on a given bus 36. The master circuit 34 is coupled to the bus 36 via a switch 38 that receives an open/close instruction from processor 32 via pin 40. A switch 42 couples the bus 36 to a power source 44 based on an open/close instruction from processor 32 via pin 46. A wake-up pin 48 on processor 32 detects a presence pulse from the slave devices when the slave devices are coupled to the housing 12.

Adapter 14 and loading unit 16 include a chip 50 and 52, respectively, that are in electrical communication with bus 36. Chips 50 and 52 are part of an authentication system that prevent unauthorized use of the surgical stapler 10. Chips 50 and 52 are capable of storing the specifications of adapter 14 or loading unit 16, such as, without limitation, cartridge size, staple arrangement, staple length, clamp-up distance, date of manufacture, expiration date, compatibility characteristics, a unique identifier (e.g., a serial number), and/or number of uses, and transmitting the specifications to handle assembly 12. In some embodiments, chips 50 and 52 include an erasable programmable read only memory ("EPROM") chip. In this manner, the handle assembly 12 may adjust the firing forces, firing stroke, and/or other operational characteristics thereof in accordance with the specifications of loading unit 16 that are transmitted from chip 52. It is further envisioned that chips 50 and 52 may include write capabilities which allow handle assembly 12 to communicate to chips 50 and 52 that the associated adapter 14 or loading unit 16 has been used, which can prevent reloading or reuse of an expended reload assembly, or any other unauthorized use. A detailed description of a surgical stapler 10 with an authentication system is provided in commonly-owned U.S. patent application Ser. No. 14/172,109 filed on Feb. 4, 2014, the contents of which is incorporated herein by reference in its entirety.

Figure 4:
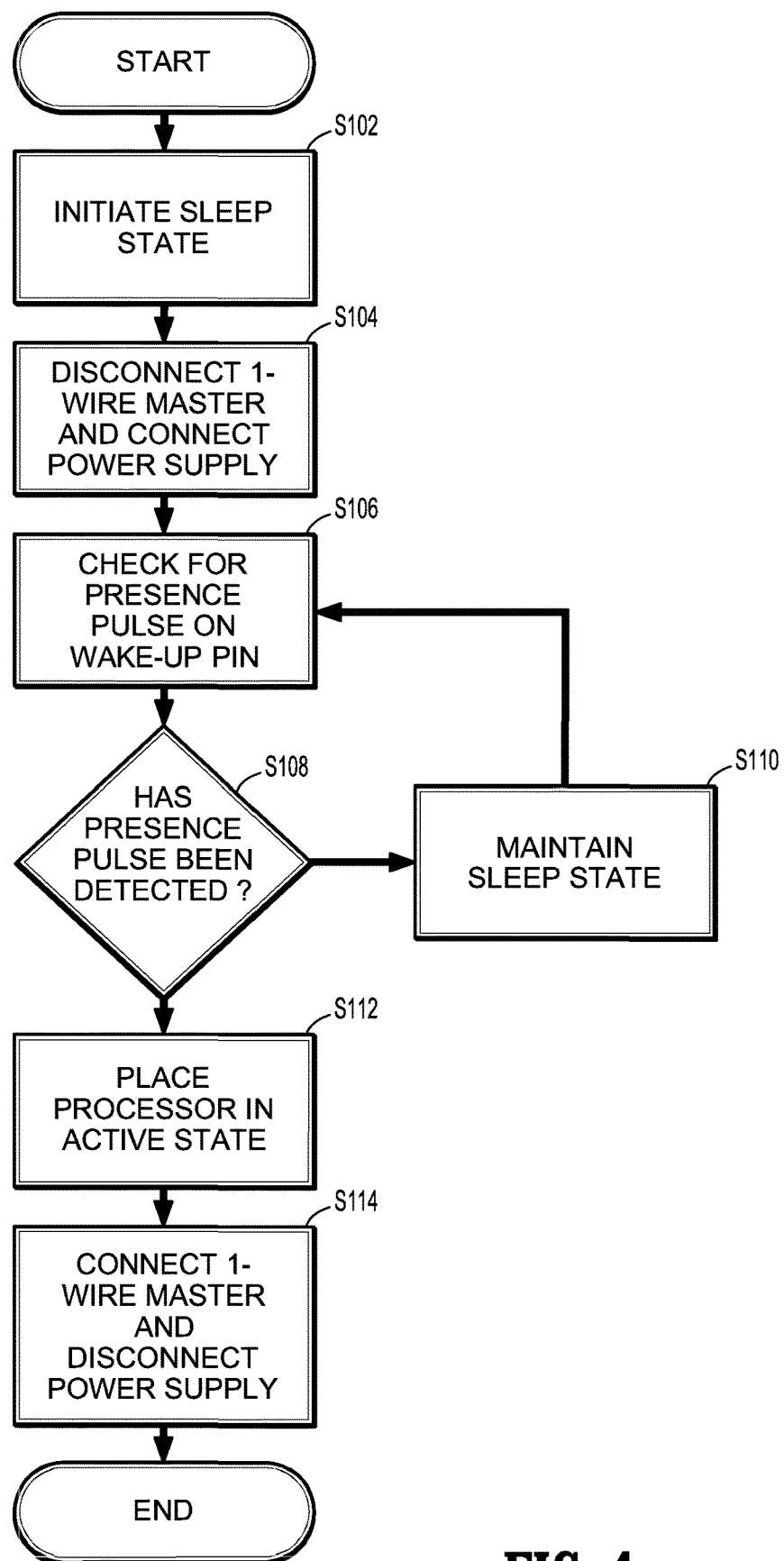
FIG. 4 is a flow chart depicting a wake-up method for the surgical stapling instrument of FIG. 1.

Turning to FIG. 4, operation of a wake-up procedure for surgical stapler 10 will be discussed with reference to FIGS. 1-3. In step s102, processor 32 is placed in a sleep state. The sleep state may be initiated based on an instruction from a clinician or if the surgical stapler 10 is inactive for a predetermined period of time. In step s104, a signal from pin 40 of processor 32 causes switch 38 to disconnect the one-wire master circuit 34 from the bus 36. Further, in step s102 a signal from pin 46 causes switch 42 to connect the bus 36 to power source 44. By connecting power source 44 to the bus, any slave device that is attached to the handle 12 can receive power in order to generate a presence pulse. In step s106, the wake-up pin 48 checks for a presence pulse from any connected slave device. The presence pulse is an automatically generated pulse (480 microseconds to ground) transmitted by the slave device after the slave device receives power. If a presence pulse is not found in step s108, the sleep state is maintained in step s110 and the procedure returns to step s106. On the other hand, if a presence pulse is detected in step s108, the procedure proceeds to step s112, where the processor 32 transitions to an active state. In step s114, the one-wire master circuit 34 is connected to the bus 36 while the power supply 44 is disconnected from the bus 36. When the processor 32 transitions from the sleep state to the active state and the one-wire master circuit 34 is connected to the bus 36, the one-wire master circuit 34 interrogates the bus for the new slave device.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method for waking up an electromechanical surgical system that is detachably couplable to an adapter, the method comprising:
   placing a processor of the electromechanical surgical system in a sleep state;
   disconnecting a one-wire master circuit from a one-wire bidirectional serial communications interface;
   connecting a power source to the one-wire bidirectional serial communications interface; and
   detecting a presence pulse from a loading unit detachably coupled to the adapter,
   wherein if the presence pulse is detected, the electromechanical surgical system is placed in an active state.

2. The method according to claim 1, wherein placing the processor of the electromechanical surgical system in the sleep state includes placing the processor of the electromechanical surgical system in the sleep state when the electromechanical surgical system is inactive for a predetermined period of time.

3. The method according to claim 1, wherein detecting the presence pulse includes detecting the presence pulse from the loading unit including a chip configured for an authentication system.

4. The method according to claim 1, wherein detecting the presence pulse includes detecting the presence pulse from the loading unit detachably coupled to the adapter in response to connecting the power source to the one-wire bidirectional serial communications interface.

5. The method according to claim 1, wherein detecting the presence pulse includes detecting the presence pulse from a single use loading unit or a multi-use loading unit.

6. The method according to claim 1, further including attaching the loading unit to the adapter.

7. The method according to claim 6, further including detachably connecting the adapter to the electromechanical surgical system.

8. The method according to claim 7, wherein connecting the power source includes connecting the one-wire bidirectional serial communications interface to a powered surgical instrument handle.

9. The method according to claim 8, wherein connecting the power source includes connecting the one-wire bidirectional serial communications interface to the powered surgical instrument handle, the powered surgical instrument handle having the processor for detecting the presence pulse.

10. A method for waking up an electromechanical surgical system that is couplable to a slave device, the method comprising:
placing a processor of the electromechanical surgical system in a sleep state;
disconnecting a one-wire master circuit from a one-wire bidirectional serial communications interface;
connecting a power source to the one-wire bidirectional serial communications interface; and
detecting a presence pulse from the slave device in response to connecting the power source to the one-wire bidirectional serial communications interface,
wherein if the presence pulse is detected, the electromechanical surgical system is placed in an active state.

11. The method according to claim 10, further including interrogating the one-wire bidirectional serial communications interface for the slave device when the electromechanical surgical system is placed in the active state.

12. The method according to claim 10, wherein detecting the presence pulse includes detecting the presence pulse from a loading unit that is attachable to an adapter.

13. The method according to claim 12, wherein detecting the presence pulse includes detecting the presence pulse from the loading unit that includes jaws configured to clamp tissue and apply staples to tissue.

14. The method according to claim 12, further including attaching the loading unit to the adapter.

15. The method according to claim 14, further including connecting the adapter to the electromechanical surgical system.

16. The method according to claim 15, wherein connecting the adapter includes connecting the adapter to the electromechanical surgical system, the electromechanical surgical system including a powered surgical instrument handle.

17. The method according to claim 16, wherein connecting the adapter includes connecting the adapter to the electromechanical surgical system, the electromechanical surgical system including the powered surgical instrument handle having the processor for detecting the presence pulse.

18. The method according to claim 17, wherein placing the processor of the electromechanical surgical system in the sleep state includes placing the processor of the electromechanical surgical system in the sleep state when the electromechanical surgical system is inactive for a predetermined period of time.

* * * * *